United States Patent [19]
Beckley

[11] Patent Number: 5,365,170
[45] Date of Patent: Nov. 15, 1994

[54] MEASUREMENT OF MAGNETIC PROPERTIES OF ELECTRICAL STEELS USING A SEARCH COIL PARTIALLY DEFINED BY A FLUID ELECTROLYTE

[75] Inventor: Philip Beckley, Newport, Wales

[73] Assignee: ORB Electrical Steels Limited, Great Britain

[21] Appl. No.: 4,906

[22] Filed: Jan. 19, 1993

[51] Int. Cl.$^5$ .................. G01R 33/12; G01R 33/02; G01N 27/72; H01F 27/28
[52] U.S. Cl. .................. 324/239; 324/258; 324/262; 336/225
[58] Field of Search .................. 324/226, 234, 238–243, 324/258, 260, 262; 336/223, 225

[56] References Cited

U.S. PATENT DOCUMENTS

| 2,477,057 | 7/1949 | Grady, Jr. | 324/239 |
| 4,558,273 | 12/1985 | Nishimura | 324/558 |

FOREIGN PATENT DOCUMENTS 1392745 4/1975 United Kingdom ............. 324/240

*Primary Examiner*—Gerard R. Strecker
*Attorney, Agent, or Firm*—Kinney & Lange

[57] ABSTRACT

A continuous method of measuring magnetic properties of a strip or sheet of an electrical steel comprises the steps of inducing in the strip or sheet electro magnetic forces and measuring the value of such induced electro magnetic forces by passing the strip or sheet continuously through a flux density detecting search coil. The search coil comprises along a part of its length a jet of fluid electrolyte.

6 Claims, 1 Drawing Sheet

MEASUREMENT OF MAGNETIC PROPERTIES OF ELECTRICAL STEELS USING A SEARCH COIL PARTIALLY DEFINED BY A FLUID ELECTROLYTE

BACKGROUND OF THE INVENTION

This invention relates to a method of and apparatus for measuring the magnetic properties of electrical steels.

Hitherto, a test known as the Epstein Square Test has been extensively used to measure and verify the magnetic properties of electrical steels. This test is carried out off-line and requires relatively narrow strips to be cut from a sheet or strip of electrical steel to be tested. It is, consequently, time consuming to perform and wasteful in terms of the steel to be tested. Also, the test is not a true indication of power loss along the complete length of the strip or sheet from which the narrow sample strip was cut.

On line systems more known in which a sheet or strip of grain oriented electrical steel is passed over or between flux inducing coils of a magnetizing system, the resulting induced magnetic flux in the strip or sheet being measured by one or more search coils positioned above and below the strip or sheet. The presence of the search coils precludes ready access to the strip or sheet under test and the close proximity of the search coil to the steel sheet or strip inhibits visual inspection of the strip or sheet surface during testing.

SUMMARY OF THE INVENTION

The present invention sets out to provide a system of measuring magnetic properties of electrical steels which overcomes, or at least alleviates, disadvantages present in existing systems.

According to the present invention in one aspect there is provided apparatus for measuring the magnetic properties of electrical steels, the apparatus comprising magnetizing means positioned below the path to be taken by a strip or sheet of electrical steel, and magnetic flux density detecting means positioned about said path, the flux density detecting means being defined in part by a coherent jet of fluid electrolyte passing from a source of such fluid to a collector.

In another aspect the present invention provides a continuous method of measuring magnetic properties of a strip or sheet of an electrical steel, the method comprising the steps of inducing in the strip or sheet electro magnetic forces and measuring the value of such induced electro magnetic forces by passing the strip or sheet continuously through a flux density detecting search coil, the search coil comprising along a part of its length a jet of fluid electrolyte.

BRIEF DESCRIPTION OF THE DRAWINGS

The invention will now be described by way of example only with reference to the accompanying diagrammatic drawings in which.

DETAILED DESCRIPTION OF THE PREFERRED EMBODIMENTS

Figure 1:
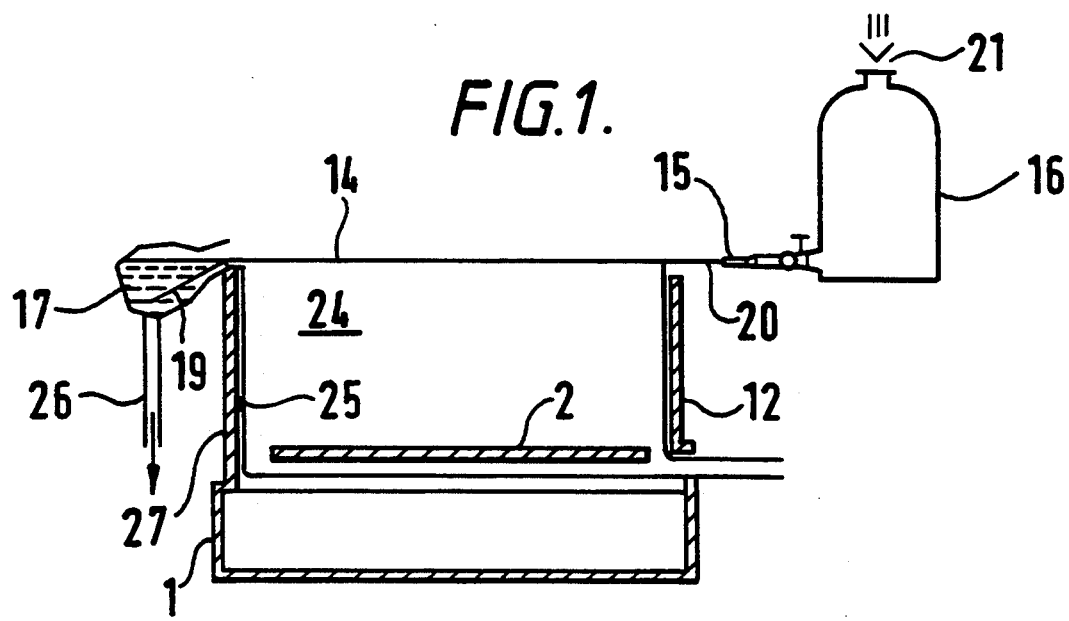
FIG. 1 is a schematic illustration partly in section of apparatus in accordance with the invention.
Figure 2:
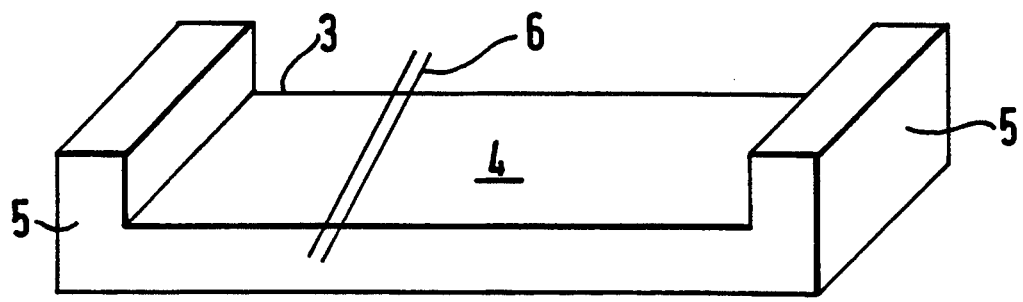
FIG. 2 is a perspective view of a yoke forming part of apparatus in accordance with the invention.

The apparatus illustrated in FIGS. 1 to 3 comprises a magnetising system 1 over which a strip or sheet (hereinafter referred to simply as "strip" for the sake of convenience) of electrical steel 2 to be tested passes in a continuous fashion. Typically the magnetising system comprises a magnetising yoke 3 as shown in FIG. 2 produced from laminations 4 of electrical steel held together by formers 5 positioned one to each side of the laminations. The yoke carries a suitable number of primary windings 6. The magnetising system operates to induce in the steel strip electro magnetic force whose strength provides a measure of the magnetic properties of the strip.

Figure 3:
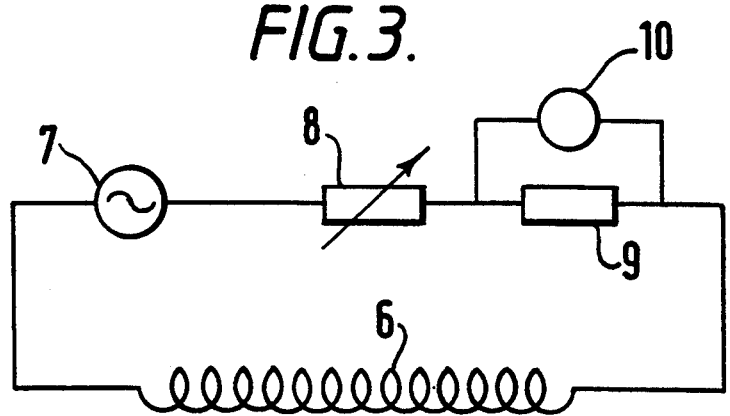
FIG. 3 is a circuit diagram of the apparatus illustrated.

A typical circuit for magnetising the strip 2 is illustrated in FIG. 3. This circuit includes a 50 Hz source 7 in series with a variable resistance box 8 and is connected to supply current to the primary windings 6 of the yoke. The induced electro magnetic force is conventionally measured by a search coil through which the strip passes, the magnetising current being measured by a meter 10 across an 0.1% shunt resistor 9. Hitherto, the search coil has taken the form of a continuous wire loop positioned about the entire circumference of the strip 2 whose magnetic properties are to be measured. As mentioned previously, the presence of such a wire loop inhibits ready access to the strip under test and visual inspection thereof.

In the present invention, the search coil is defined only in part by a conventional wire loop 12, the upper extent of the search coil being defined by a coherent jet of fluid electrolyte 14 issuing from a discharge nozzle 15 of an electrolyte containing vessel 16. The discharge nozzle 15 is typically constructed from aluminum, although other suitable materials may be employed. The fluid electrolyte is collected in a vessel 17 spaced from the vessel 16 and the electrical contacts with the wire section of the search coil are effected by immersing one end 19 of the wire loop 12 in the collected electrolyte present in the vessel 17 and attaching the other end 20 of the wire loop to the nozzle 15.

The electrolyte fluid present in the vessel 16 is selected to provide the dual properties of electrical conductivity and compatibility with the grades of grain oriented electrical steel to be tested. The latter is important because, inevitably, some electrolyte will make contact with the strip surface. Suitable electrolytes include an aqueous solution of ammonia or of citric acid. The electrolyte fluid present in the vessel 16 is subjected to a controlled air pressure via a valve 21, the pressure being at least sufficient to cause the fluid electrolyte to be projected as a continuous coherent stream across the space between the nozzle 15 and the collecting vessel 17 thereby completing the search coil loop. Both vessels 16 and 17 are earthed.

The wire section 12 of the search coil is located within an open channel 24 situated below the electrolyte jet 14, the wire 12 being secured to the conducting walls 27 of the channel by, for example, low resistance copper tape 25. As will be understood from the foregoing, the wire coil 12 and the jet 14 of fluid electrolyte together define the search coil through which the steel strip under test passes. The presence of the fluid electrolyte in place of a solid wire facilitates ready access to the strip.

In use, fluid electrolyte present in the vessel is projected as a continuous coherent stream through the nozzle 15 and across the space between the vessels 16, 17. Fluid collected in the vessel 17 passes to a drain via a discharge pipe 26. Alternatively, the fluid may be collected and returned to the vessel 16 for re-use. The pressure imparted to the fluid within the vessel 16 is sufficient to ensure that the resulting continuous jet is coherent along its entire length.

To investigate the invention, a 3% grain oriented sample of size 600 mm×115 mm×0.32 mm was magnetised to 1.5 and 1.7 Tesla using the apparatus described. At each of the two induction levels, fluid electrolyte projection lengths of 11 cm and 14 cm were employed to observe the effect of the projection length on the conductivity and scattering of the solution.

The results of this investigation showed that with both projection lengths a clear signal was received from the non-solid search coil of the invention closely followed the trend and magnitude of a comparative reference signal.

The investigation also showed that best results were obtained when the vessel 16 was full and the outflow of fluid from the nozzle 15 was such as to maintain the electrolyte level within the vessel substantially constant.

It was found that at start up the liquid electrolyte jet quickly established the required signal from the search coil and that, provided the electrolyte jet remained coherent along its length the signal received from the coil provided an accurate measure of the magnetic properties of the strip under test.

It will be understood that the foregoing is merely exemplary of apparatus for and a method of measuring magnetic properties of electrical steel in accordance with the invention and that modifications can readily be made thereto without departing from the true scope of the invention. For example, magnetisation can be maintained sinusoidal by use of the magnetisation signal within a system employing a negative feedback amplifier as magnetisation source.

What is claimed is:

1. An apparatus for measuring the magnetic properties of electrical steels, the apparatus comprising:
   means for inducing in a strip or sheet of electrical steel a magnetising electromagnetic force whose strength provides a measure of the magnetic properties of the strip or sheet;
   a search coil through which the magnetized strip or sheet passes and whose upper extent is defined by a coherent jet of fluid electrolyte; and
   means coupled to the search coil for measuring the electromagnetic force induced within the strip or sheet.

2. The apparatus as claimed in claim 1, wherein the means for inducing an electromagnetic force within the said strip of sheet comprises a magnetising yoke produced from laminations of electrical steel retained within formers positioned one to each side of the laminations.

3. The apparatus as claimed in claim 1, wherein the jet of fluid electrolyte is discharged through a electrically conductive discharge nozzle of a collecting vessel.

4. The apparatus as claimed in claim 1, wherein the fluid electrolyte comprises an aqueous solution of anomia.

5. The apparatus as claimed in claim 1, wherein the fluid electrolyte comprises citric acid.

6. A continuous method of measuring magnetic properties of a strip or sheet of an electrical steel, the method comprising the steps of:
   inducing in the strip or sheet magnetising electromagnetic forces whose strength provides a measure of a magnetic property of the strip or sheet;
   passing the magnetized strip or sheet through a search coil whose upper extent is defined by a coherent jet of fluid electrolyte; and
   measuring, by means of the search coil, the electromagnetic force induced within the strip or sheet to provide a measure of the magnetic properties of the strip or sheet.

* * * * *

UNITED STATES PATENT AND TRADEMARK OFFICE
CERTIFICATE OF CORRECTION

PATENT NO. : 5,365,170
DATED : November 15, 1994
INVENTOR(S) : PHILIP BECKLEY

It is certified that error appears in the above-indentified patent and that said Letters Patent is hereby corrected as shown below:

Col. 4, lines 5, 16 and 31, delete "magnetising", insert -- magnetizing--

Signed and Sealed this

Eleventh Day of April, 1995

*Attest:*

BRUCE LEHMAN

*Attesting Officer*   Commissioner of Patents and Trademarks